United States Patent [19]

Jensen

[11] Patent Number: 4,778,446
[45] Date of Patent: Oct. 18, 1988

[54] WOUND IRRIGATION AND/OR DRAINAGE DEVICE

[76] Inventor: Ole R. Jensen, 646 Orangeburg Rd., River Vale, N.J. 07675

[21] Appl. No.: 513,740

[22] Filed: Jul. 14, 1983

[51] Int. Cl.⁴ .............................................. A61M 1/00
[52] U.S. Cl. ...................................... 604/27; 604/317
[58] Field of Search .................................. 604/27-29, 604/48, 73, 289, 277, 332-345, 317; 128/760, 767, 762, 157; 141/59

[56] References Cited

U.S. PATENT DOCUMENTS

| | | | |
|---|---|---|---|
| Re. 29,319 | 7/1977 | Nordby | 128/275 |
| 3,042,041 | 7/1962 | Jascalevich | 604/277 |
| 3,121,021 | 2/1964 | Copeland | 117/122 |
| 3,123,074 | 3/1964 | Turner | 604/332 |
| 3,339,546 | 9/1967 | Chen | 128/156 |
| 3,568,675 | 3/1971 | Harvey | 128/275 |
| 3,874,387 | 4/1975 | Barbieri | 128/325 |
| 3,972,328 | 8/1976 | Chen | 128/156 |
| 4,023,569 | 5/1977 | Wavnecke et al. | 128/154 |
| 4,192,785 | 3/1980 | Chen et al. | 260/17.4 |
| 4,224,941 | 9/1980 | Stivala | 128/207.26 |
| 4,250,882 | 2/1981 | Adair | 128/275 |
| 4,468,227 | 8/1984 | Jensen | 604/327 |

FOREIGN PATENT DOCUMENTS

| | | |
|---|---|---|
| 0063898 | 11/1982 | European Pat. Off. . |
| 641061 | 8/1950 | United Kingdom .............. 604/289 |
| 1549756 | 8/1979 | United Kingdom . |
| 2099308 | 12/1982 | United Kingdom . |

Primary Examiner—C. Fred Rosenbaum
Assistant Examiner—J. L. Kruter
Attorney, Agent, or Firm—James & Franklin

[57] ABSTRACT

To prevent contact with the wound, a semi-rigid cylindrical hollow open-ended collar is mounted to an adhesive label by a flexible sheet. The sheet is sealed to the periphery of the lower end of the collar and ring-welded or adhesively attached to the surface of the label. The periphery of the sheet has an outwardly extending accordion-like section which expands to permit the label to accommodate the contours of the body. Irrigation ports may be situated in the collar wall. A drain port may be situated in the flexible sheet. The upper open end of the collar is designed to receive a removable cover which may have a transparent portion. Alternatively, the cover member may be provided with a flexible section surrounding an opening adapted to receive a catheter.

22 Claims, 5 Drawing Sheets

F I G. 6
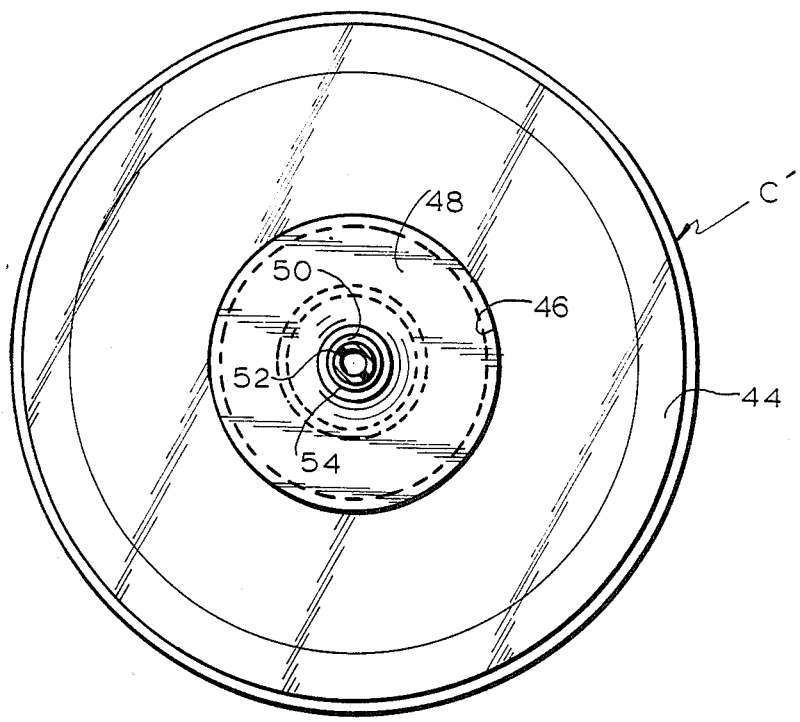
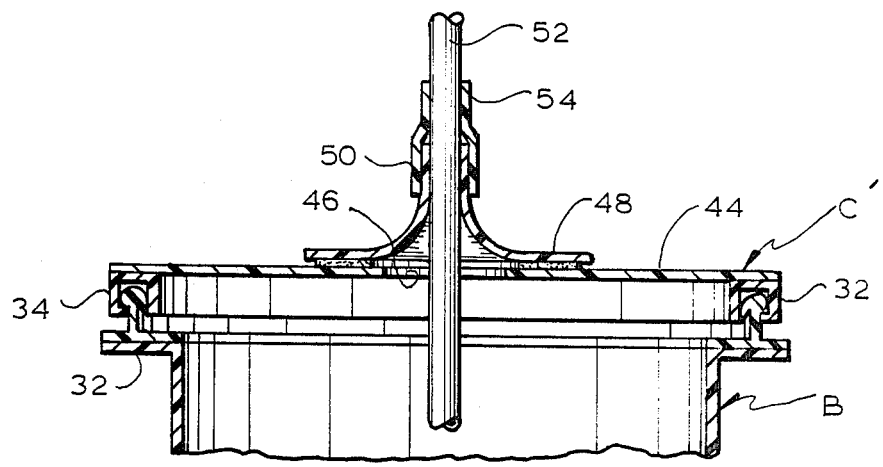
F I G. 7

WOUND IRRIGATION AND/OR DRAINAGE DEVICE

The present invention relates to wound irrigation and/or drainage devices and, more particularly, to a wound irrigation and/or drainage device which utilizes a self-supporting collar to protect the wound from contact, flexible mounting means which permits the adhesive-backed member to more readily accommodate the contours of the body, and a novel cover member designed to permit insertion of a catheter into the wound.

It is preferable in the treatment of certain types of wounds, particularly postoperative wounds, and certain skin disorders such as ulcers, burns, sores, and the like, to irrigate the affected region with fluid, such as antiseptic liquid or hyperbaric oxygen. In addition, certain types of wounds require periodic drainage. Various types of devices have been proposed for these applications. Certain of these devices are designed to be mounted to the patient's body, surrounding the afflicted region, for an extended period of time to permit periodic irrigation and/or drainage. It is often necessary that the wound be visible for purposes of observation and, accordingly, devices of this type are normally provided with a transparent portion which permits observation of the affected region.

One device of this type which is commercially available is described in British Patent Specification No. 1,549,756, entitled "A Wound Irrigating Device." That device includes a rectangular, transparent, flexible plastic cover mounted on a rim with an adhesive back. The rim is situated on the skin of the patient surrounding the wound such that the wound is aligned with the hollow chamber defined by the cover. An entry port and an exit port are provided for irrigating fluid. A conventional D.U. infusion set may be connected to the entry port, to permit a fluid such as hydrogen peroxide to be flushed through the device. The plastic cover may be transversely ribbed to increase the flexibility of the device in the longitudinal direction.

In the absence of any substantial external force applied to the cover, the cover will normally retain its shape with the upper surface at a location spaced from the wound, thereby preventing contact with the wound.

While the cover, and particularly the transversely ribbed version thereof, is designed to flex relatively easily in the longitudinal direction, flexing in the transverse direction will cause the cover to collapse. Also, this device can normally be used only on relatively flat areas of the body as it does not easily conform to curved body contours. Moreover, since the device is elongated in the longitudinal direction, it is suitable for use only with wounds which are similarly shaped. Thus, the instances in which this device can be utilized effectively are limited.

A commercially available drainage device is described in British Patent Application No. 2,099,308 which eliminates some of the above disadvantages. This device is formed of highly flexible liquid impermeable sheets of material and includes a rather large circular opening which is adapted to align with the wound. The flexibility of this device permits it to be used on areas of the body with curved contours. The large circular opening permits the device to be used with wounds of a variety of different shapes.

The device includes a flexible pouch with top and bottom walls and pleated side walls which permit the pouch to expand. The top wall includes an access opening having a flanged locking ring of flexible plastic extending thereabout. A removable closure cap is attached to the access opening and has a rim with circumferential locking ribs to seal the cap on the flanged locking ring of the pouch. The pouch is elongated and has a drainage port at one end. A portion of the underside of the pouch is coated with a layer of surgical hypoallergenic pressure-sensitive adhesive to permit mounting of the device to the skin.

The major problem with the device disclosed in British Patent Application No. 2,099,308 is that the flexibility of the pouch permits the upper surface thereof, and particularly the undersurface of the closure cap, to be in contact with the wound. Such contact is normally contra-indicated, particularly immediately after surgery. Accordingly, this product also has limited usefulness.

It is, therefore, a prime object of the present invention to provide a wound irrigation and/or drainage device which prevents contact with the wound and, at the same time, is flexible enough to conform to the contours of the patient's body.

It is another object of the present invention to provide a wound irrigation and/or drainage device which includes a rigid or semi-rigid collar member which prevents contact with the wound, even if substantial external forces are applied thereto.

It is another object of the present invention to provide a wound irrigation and/or drainage device wherein the collar member is mounted in a manner which permits enhanced flexibility.

It is another object of the present invention to provide a wound irrigation and/or drainage device usable with irregularly shaped wounds.

It is another object of the present invention to provide a wound irrigation and/or drainage device which includes a novel cover member through which a catheter or similar tube may be inserted.

It is another object of the present invention to provide a wound irrigation and/or drainage device in which the cover member includes means for sealing the surface thereof with the inserted catheter tube.

It is another object of the present invention to provide a wound irrigation and/or drainage device comprised of relatively simple, inexpensive parts which cooperate reliably to permit extended usage.

In accordance with the present invention, a wound irrigation and/or drainage device is provided. The device comprises a flexible adhesive-backed member having an aperture adapted to align with the wound when the device is mounted on the wearer. A substantially hollow body member is provided having first and second open ends. Means are provided for mounting one of the ends of the body member to the adhesive member, in alignment with the aperture. A cover member is provided. Means are provided for releasably mounting the cover member to the other end of the body member to form a substantially fluid-tight chamber in communication with the aperture. At least one fluid port is provided in the chamber. The body member comprises self-supporting means to prevent contact with the wound.

The self-support means comprises a substantially cylindrical rigid or semi-rigid element, preferably in the form of an upstanding wall. The port may be situated in the wall.

The means for mounting the body member to the adhesive member comprises a substantially flexible sheet mounted to the end of the body member. The sheet is joined to the adhesive member so as to surround the aperture. Preferably, the sheet is joined to the adhesive member at a point spaced from the aperture. The port may be situated in the flexible sheet.

Preferably, the sheet comprises expandable means and is mounted to the periphery of the element. The expandable means comprises an accordion-like fold which extends outwardly of the periphery of the element and, thereafter, extends inwardly to the adhesive member.

The cover member preferably has a transparent portion. Alternatively, the cover member may have a surface with an opening adapted to receive a tube therethrough. In this embodiment, the cover member comprises means for sealing the surface to the tube. In addition, means may be provided for joining the sealing means to the tube. Such means may take the form of an adhesive tape or the like.

The cover member comprises a relatively rigid portion to which the releasable mounting means is mounted, a relatively flexible portion and an opening in the flexible portion adapted to receive the tube. Preferably, the relatively rigid portion has a substantially annular configuration with a relatively large central aperture. The flexible portion is situated within the central aperture.

In one embodiment, the support means is substantially circular. In another embodiment, the support means is substantially oval.

To these and to such other objects which may hereinafter appear, the present invention relates to a wound irrigation and/or drainage device, as set forth in the following specification and recited in the annexed claims, taken together with the accompanying drawings, wherein like numerals refer to like parts, and in which:

FIG. 6 is a plan view of an alternate embodiment of the cover member, designed to accept a catheter tube;

FIG. 7 is a cross-sectional view of the cover illustrated in FIG. 6; and

Figure 1:
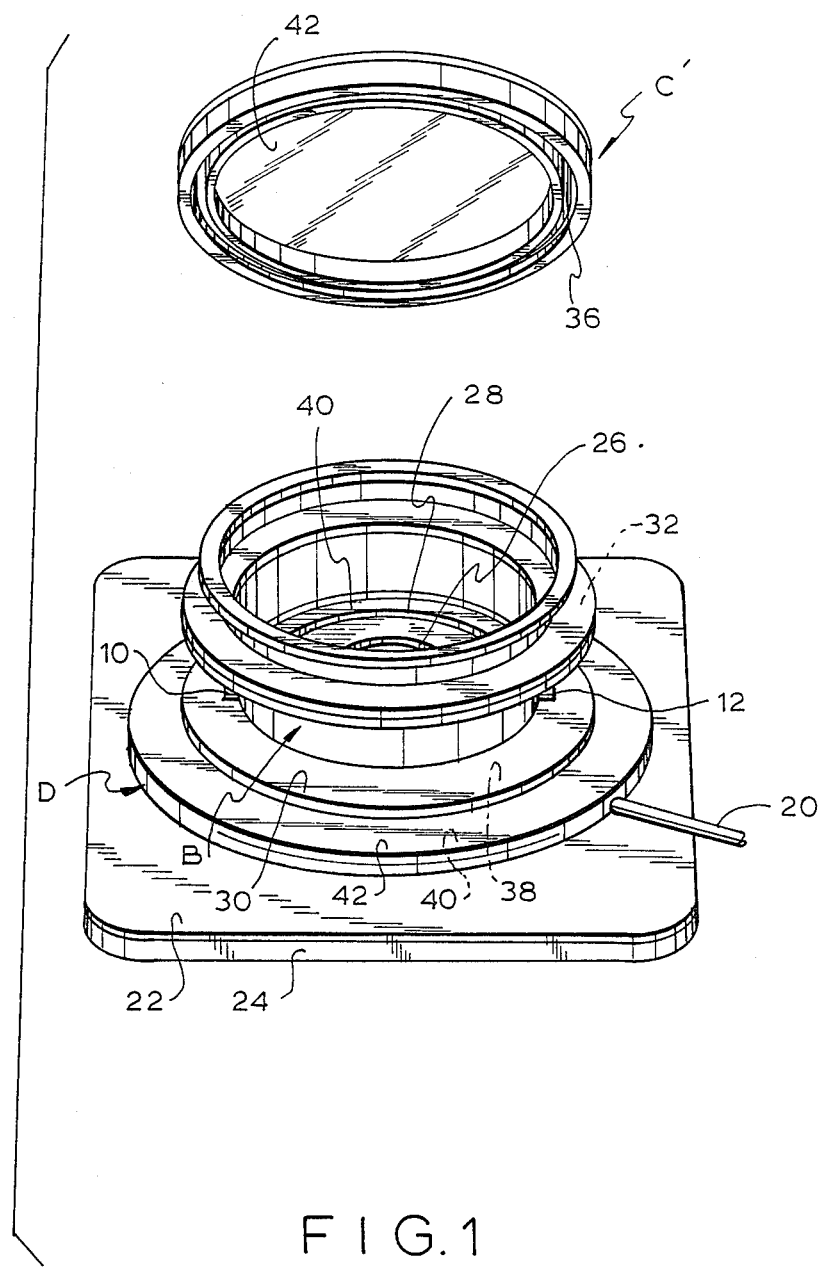
FIG. 1 is an exploded isometric view of the wound irrigation and/or drainage device of the present invention.

As illustrated in FIGS. 1–4 and 8, the wound irrigating and/or drainage device of the present invention comprises an adhesive-backed label, generally designated A, designed to be affixed to the skin of the patient in the afflicted region. Mounted to the upper surface of adhesive-backed label A is a cylindrical hollow collar, generally designated B, composed of rigid or semi-rigid material, preferably plastic. Collar B has a lower open end which faces label A and an upper open end upon which a cover member, generally designated C, is releasably mounted. The lower open end of collar B is mounted to label A by flexible mounting means, generally designated D.

Preferably, collar B is formed by molding rigid or semi-rigid plastic material and includes an integral inlet port 10 and outlet port 12. Tubes (not shown) can then be connected to these ports to permit the introduction of fluid into the interior of collar B and the removal of fluid from the interior of collar B, so as to irrigate the wound. If the device is being employed only to drain a wound, then ports 10 and 12 would be sealed by fluid-tight plugs (not shown). In addition, a drainage tube 20 is preferably welded into position in flexible mounting means D to permit drainage of fluid from the wound.

Label A, as shown in FIGS. 1-4, comprises a base 22 composed of a thin film of polymeric material such as polyethylene or a breathable non-woven material such as a spun-bonded polyester and a medical grade adhesive layer 24 on the undersurface of base 22. Adhesive layer 24 consists of materials known to be suitable for use on the human body. Preferably, layer 24 is formed as a homogeneous blend of one or more pressure-sensitive viscous materials such as polyisobutylene having intermittently dispersed therein one or more water-soluble or swellable hydrocolloid gums and may also include one or more thermoplastic elastomers and/or one or more water swellable cohesive strengthening agents, as described by Chen in U.S. Pat. No. 3,339,546 and Chen et al. in U.S. Pat. No. 4,192,785. For increased comfort, adhesive layer 24 can be formulated so as to be microporous as described in European Patent Application No. 82.301925.2, and entitled "Microporous Adhesive Tape." A microporous acrylic adhesive such as that taught by Copeland in U.S. Pat. No. 3,121,021 can also be employed as adhesive layer 24. Also, label A may include a layer of foam between base 22 and adhesive layer 24, as taught by Chen in U.S. Pat. No. 3,972,328.

Figure 8:
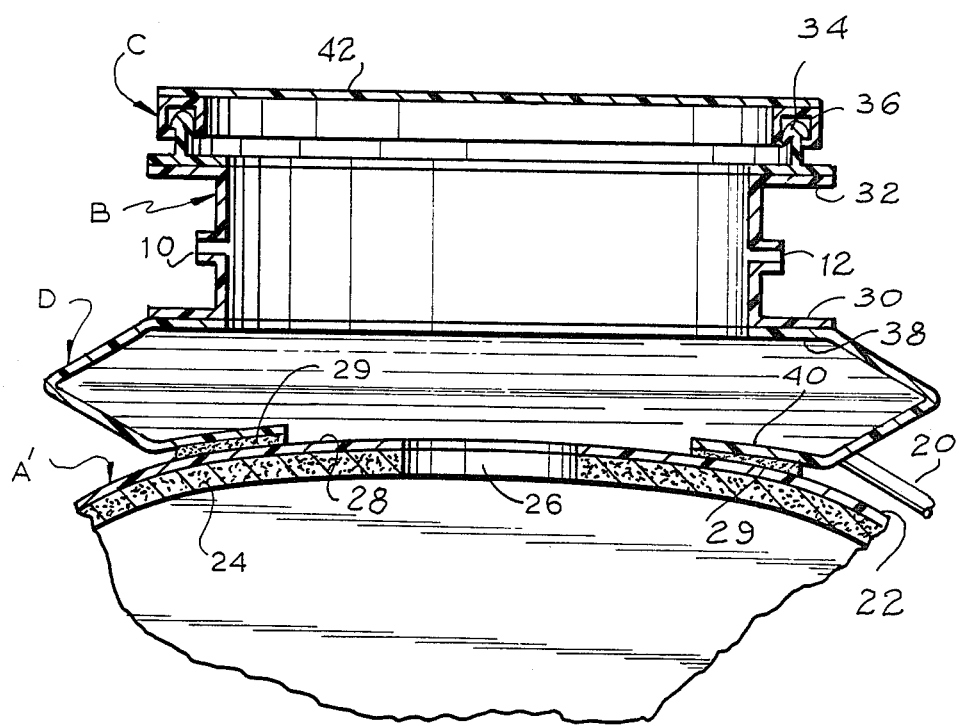
FIG. 8 is a view similar to FIG. 2, showing an alternate embodiment of the adhesive label.

Label A', as shown in FIG. 8, comprises medical grade adhesive layer 24 formed as described above and adhesive layer 29 which bonds flexible mounting means D to layer 24. Adhesive layer 29 need not be of medical grade and can be a conventional acrylic type adhesive.

Adhesive-backed labels A and A' are provided with a precut central aperture 26 of relatively small dimension. As is well known in the art of ostomy devices, the labels are designed such that aperture 26 may be enlarged by the physician or nurse, to the shape of the wound, prior to application of the adhesive-backed label to the skin of the patient. In the case of label A, aperture 26 can be enlarged up to the ring weld 28 which joins base 22 of adhesive label A to flexible mounting means D. In the case of label A', aperture 26 can be enlarged almost to the edge of adhesive layers 29 and 24. Accordingly, the structure of the present invention permits a rather large aperture to be formed in the labels, permitting the device to accommodate even relatively large, irregularly shaped wounds, not possible in the prior art devices.

Collar B is preferably made of rigid or semi-rigid plastic material. The walls of collar B must have sufficient strength such that collar B can withstand any external force which the patient is likely to encounter without collapsing. Thus, the thickness of the walls of collar B and the strength of the material of which it is composed must be selected such that the collar is entirely self-supporting even when external forces are exerted thereto.

Extending outwardly from the lower edge of collar B is a flange 30. The undersurface of flange 30 is joined to the upper surface of flexible mounting means D by any conventional method, such as by welding or by adhesive, so as to form a fluid-tight seal therebetween.

The upper portion of collar B has an outwardly extending flange 32 similar to flange 30. Joined to the upper surface of flange 32, by any conventional method such as adhesive or the like, is a ring-like male interengaging part 34. Interengaging part 34 is situated to releasably engage a ring-like female interengaging part 36 which forms the lower rim of cover member C. Interengaging parts 34 and 36 are of conventional design and are constructed to form a fluid-tight seal. The male and female interengaging parts may be interchanged such that the female interengaging part is mounted on collar B and the male interengaging part is mounted on cover member C, if desired.

Figure 3:
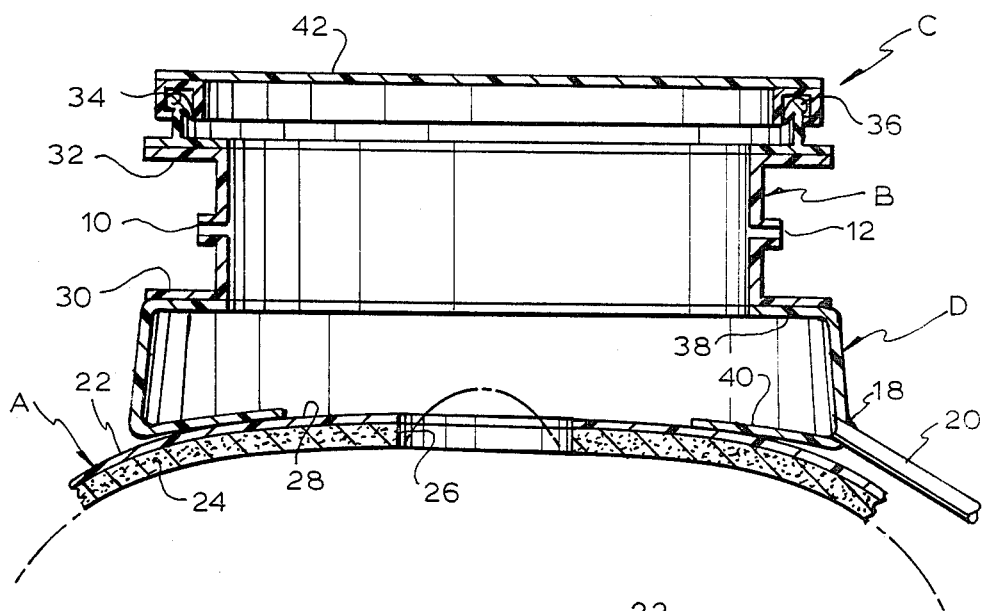
FIG. 3 is a cross-sectional view of the assembled device of the present invention as same is mounted on the skin of the wearer.

As is best illustrated in FIG. 3, adhesive-backed label A is often affixed to the patient's body in a region which is not planar, that is, may be curved or rounded. While the base 22 of the label A is itself quite flexible, if the label A were affixed directly to collar B, the flexibility of label A, and therefore its ability to conform to the contours of the body, would be severely limited because of the rigidity of collar B. Accordingly, collar B is mounted to label A by flexible mounting means D such that collar B does not reduce the flexibility of label A and, thus, its ability to conform to the contours of the body.

Figure 2:
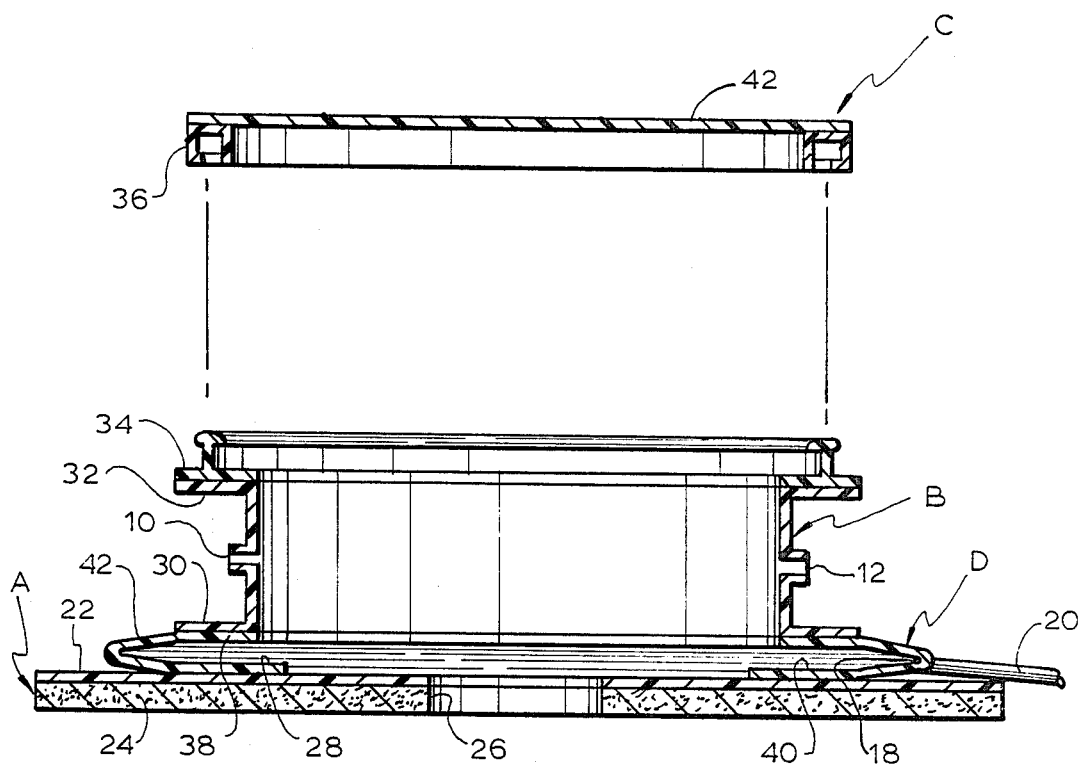
FIG. 2 is an exploded cross-sectional view of the device illustrated in FIG. 1.

Mounting means D is composed of a thin, flexible, fluid-impervious sheet which has an upper section 38 affixed to the lower surface of flange 30 by any conventional means such as by welding or by adhesive, to form a fluid-tight seal. The lower section 40 of means D is affixed to the upper adhesive surface 29 of label A' or to the upper surface of base 22 of label A by means of ring weld 28. Between sections 38 and 40 of means D is an expandable section 42 which has an accordion-like fold therein. Section 42 may expand as illustrated in FIG. 3, to permit label A to be flexed in accordance with the contours of the body. When collapsed, as seen in FIG. 2, section 42 of means D extends outwardly of the periphery of collar B and inwardly towards label A. Drain tube 20 is welded into section 42 of means D such that if the patient is lying down, fluid from the wound will collect at the lowest portion of means D and be removed therefrom through drain tube 20.

Cover member C is normally provided with a transparent window portion 42 to permit observation of the wound. Cover member C may be removed from collar B to permit access to the wound without removing the adhesive-backed label A from the skin of the patient.

Figure 4:
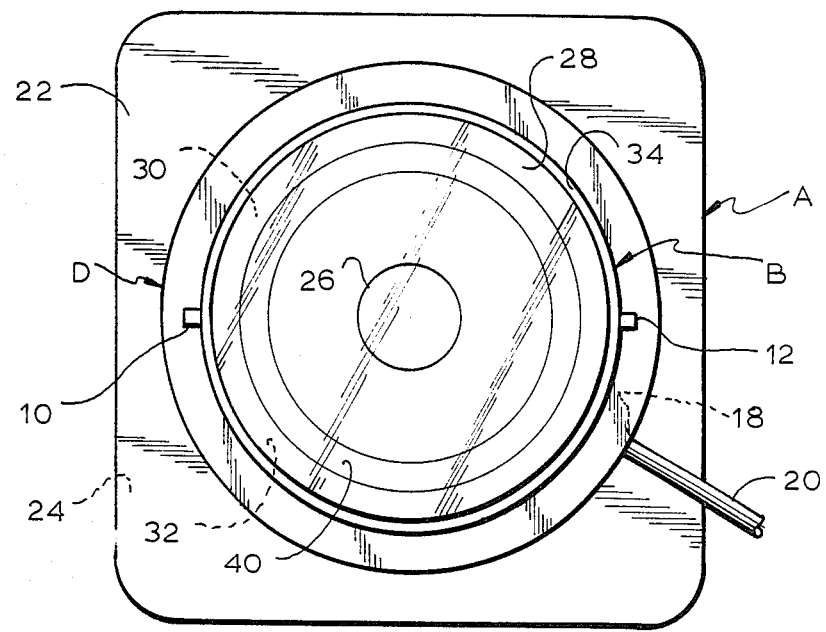
FIG. 4 is a plan view of the first preferred embodiment of the present invention having a round body member.
Figure 5:
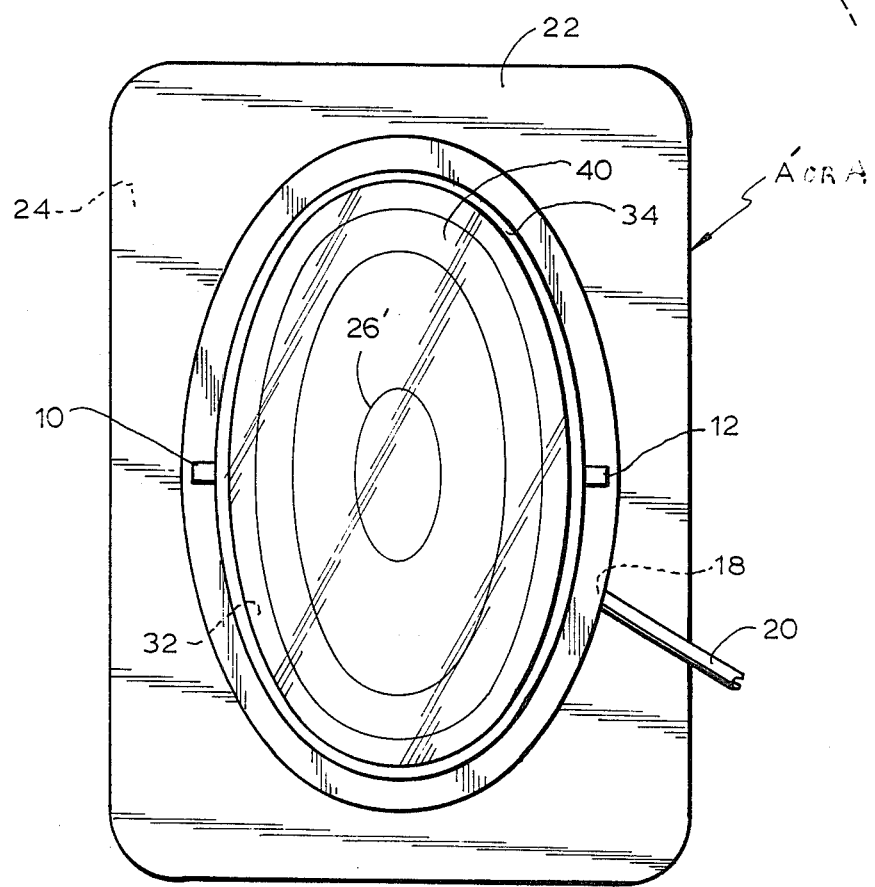
FIG. 5 is a plan view of a second preferred embodiment of the present invention having an oval shaped body member.

As illustrated in FIG. 4, the first preferred embodiment of the present invention includes a collar B which is circular in configuration. In spite of the fact that the present invention permits the enlargement of aperture 26 in label A to a relatively large extent, there are certain cases where a wound, particularly the result of surgery, is so elongated that aperture 26 cannot be enlarged enough to accommodate same. In those instances, the second preferred embodiment of the present invention, as illustrated in FIG. 5, may be utilized. As seen in FIG. 5, collar B' and its various parts, as well as aperture 26' in label A', are each provided with a substantially oval shape designed to accommodate extremely elongated wounds. All other parts of the second preferred embodiment shown in FIG. 5 are functionally and structurally the same as those described above.

FIGS. 6 and 7 illustrate an alternative cover member C' which may be utilized with the device of the present invention. Cover member C' is designed for use in those instances in which a drainage tube or catheter must be inserted directly into the wound.

In cover member C', transparent portion 42 is replaced by an outer annular section 44 of relatively rigid plastic, either opaque or transparent, with a relatively large central opening 46. Affixed to the upper surface of section 44, adjacent opening 46, is a circular member 48 composed of flexible plastic or the like. Member 48 has a central opening 50 therein. The diameter of central opening 50 in member 48 is smaller than the outer diameter of the catheter tube 52. Because of the flexibility of member 48 and the size of aperture 50 therein, when catheter tube 52 is inserted into aperture 50 from the bottom of cover member C', the walls of member 48 will be directed upwardly and tightly against the exterior of the catheter tube 52. In order to seal member 48 to the exterior of catheter tube 52, a strip of adhesive tape 54 or the like may be used to insure that a fluid-tight seal is obtained and, in addition, to prevent catheter tube 52 from being accidentally pulled from the wound.

It will now be appreciated that the present invention relates to a wound irrigation and/or drainage device which is both rigid enough to prevent contact with the wound, even if external forces such as the weight of a blanket or the like are exerted thereon and, at the same time, is flexible enough to be worn comfortably and to conform to the contours of the patient's body. These objects are achieved by utilizing a rigid or semi-rigid collar member which is entirely self-supporting and which will resist collapsing due to external forces. The flexibility of the adhesive-backed label is not restricted by the rigidity of the collar due to the flexible means which are utilized to mount the collar on the label. Moreover, the structure of the present invention permits same to be utilized with rather large wounds because the label aperture can be enlarged to a relatively large extent. A second preferred embodiment of the invention is provided particularly for use with elongated wounds.

The present invention can also be utilized with a specially designed cover member which permits a catheter tube to be inserted directly into the wound. This specially designed cover member comprises an extremely flexible member which permits the insertion of the tube therethrough and will tightly adhere to the exterior surface of the tube. Further, the member may be affixed to the tube in a manner which permits a fluid-tight seal to be formed and which prevents the accidental retraction of the tube.

While only a limited number of preferred embodiments of the present invention have been disclosed herein for purposes of illustration, it is obvious that many modifications and variations could be made thereto. It is intended to cover all of these variations and modifications which fall within the scope of the present invention, as defined by the following claims:

I claim:

1. A wound irrigation and/or drainage device comprising a flexible microporous adhesive-backed member having an aperture adapted to align with the wound when the device is mounted on the body of the wearer, a substantially rigid hollow cylindrical member having first and second open ends, expandable means for mounting one of said ends of said cylindrical member to said adhesive member, in alignment with said aperture, a cover member, means for releasably mounting said cover member to said other end of said cylindrical member to form a substantially fluid-tight chamber in communication with said aperture, at least one fluid port in said chamber, said cylindrical member being sufficiently self-supporting to maintain said cover member at a position remote from the wound.

2. The device of claim 1, wherein said cylindrical member comprises a substantially self-supporting upstanding wall.

3. The device of claim 2, wherein said port is situated in said wall.

4. The device of claim 3, further comprising a second port in said wall.

5. The device of claim 1, wherein said expandable means for mounting said body member to said adhesive member comprises a substantially flexible sheet, one end of which is mounted to said one end of said body member and the other end of which is joined to said adhesive member.

6. The device of claim 5, wherein said expandable means comprises an accordion-like fold.

7. The device of claim 6, wherein said fold extends outwardly of said body member.

8. The device of claim 5, wherein said sheet is joined to said adhesive member so as to surround said aperture.

9. The device of claim 5, wherein said sheet is joined to said adhesive member at a point spaced from said aperture.

10. The device of claim 5, wherein said port is in said flexible sheet.

11. The device of claim 5, wherein said sheet is joined to said adhesive member by a ring weld.

12. The device of claim 5, wherein said sheet is joined to said adhesive member by a substantially annular adhesive layer.

13. The device of claim 1, wherein said cover member has a transparent portion.

14. The device of claim 1, wherein said cover member has a surface with an opening adapted to receive a tube therethrough.

15. The device of claim 14, wherein said cover member comprises means for sealing said surface to the tube.

16. The device of claim 15, further comprising means for joining said sealing means to said tube.

17. The device of claim 1, wherein said cover comprises a relatively rigid portion to which said releasable mounting means is joined, a relatively flexible portion and an opening in said flexible portion adapted to receive a tube therethrough.

18. The device of claim 17, wherein said relatively rigid portion has a substantially annular configuration with a central aperture.

19. The device of claim 18, wherein said flexible portion is situated in said central aperture.

20. The device of claim 1, wherein said body member is substantially circular.

21. The device of claim 1, wherein said body member is substantially oval.

22. The device of claim 2, wherein said expandable means for mounting said body member to said adhesive member comprises a substantially flexible sheet mounted to said one end of said body member, said sheet being joined to said adhesive member.

* * * * *

UNITED STATES PATENT AND TRADEMARK OFFICE
CERTIFICATE OF CORRECTION

PATENT NO. : 4,778,446

DATED : Oct. 18, 1988

INVENTOR(S) : Ole R. Jensen

It is certified that error appears in the above-identified patent and that said Letters Patent is hereby corrected as shown below:

On the title page, insert --[73] Assignee: E.R. SQUIBB & SONS, INC., Princeton, N.J.--.

Signed and Sealed this

Twenty-eighth Day of November 1989

*Attest:*

JEFFREY M. SAMUELS

*Attesting Officer*     *Acting Commissioner of Patents and Trademarks*